US012629115B2

(12) United States Patent
Sato et al.

(10) Patent No.: US 12,629,115 B2
(45) Date of Patent: May 19, 2026

(54) STRUCTURE FOR FORMING A PARALLEL X-RAY BEAM, X-RAY DIAGNOSTIC APPARATUS, AND METHOD

(71) Applicant: CANON MEDICAL SYSTEMS CORPORATION, Tochigi (JP)

(72) Inventors: Daisuke Sato, Utsunomiya (JP); Tomio Maehama, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 173 days.

(21) Appl. No.: 18/057,940

(22) Filed: Nov. 22, 2022

(65) Prior Publication Data

US 2023/0165549 A1      Jun. 1, 2023

(30) Foreign Application Priority Data

Nov. 26, 2021    (JP) ................................. 2021-192395

(51) Int. Cl.
*A61B 6/40* (2024.01)
*A61B 6/00* (2006.01)
(Continued)

(52) U.S. Cl.
CPC .............. *A61B 6/4035* (2013.01); *A61B 6/06* (2013.01); *A61B 6/4291* (2013.01); *A61B 6/4429* (2013.01); *A61B 6/4435* (2013.01); *A61B 6/4452* (2013.01); *A61B 6/482* (2013.01); *A61B 6/5258* (2013.01); *A61B 6/5282* (2013.01); *G21K 1/025* (2013.01); *G21K 1/10* (2013.01)

(58) Field of Classification Search
CPC ......... A61B 6/032; A61B 6/06; A61B 6/4035;
A61B 6/4291; A61B 6/44; A61B 6/4405; A61B 6/4429; A61B 6/4435; A61B 6/4452; A61B 6/5258; A61B 6/5282; A61B 6/035; A61B 6/482; G21K 1/02; G21K 1/025; G21K 1/04; G21K 1/10
USPC ..... 378/7, 62, 147, 149, 154, 189, 196–198, 378/145, 156–159, 196–198
See application file for complete search history.

(56) References Cited

U.S. PATENT DOCUMENTS 4,688,242 A * 8/1987 Ema ....................... G21K 1/025
378/7
4,761,802 A * 8/1988 Kiri .......................... H04N 5/32
378/146

(Continued)

FOREIGN PATENT DOCUMENTS

JP      2000-354593 A      12/2000
JP      2003018463 A  *   1/2003   ............... A61B 6/06
(Continued)

OTHER PUBLICATIONS

An English translation of JP2014050737A by Patent Translate (Year: 2024).*

(Continued)

*Primary Examiner* — Allen C. Ho
(74) *Attorney, Agent, or Firm* — Oblon, McClelland, Maier & Neustadt, L.L.P.

(57) ABSTRACT

A structure according to an embodiment is disposed between an X-ray emitter and a subject, and includes a scatterer configured to scatter X-rays emitted from the X-ray emitter, and a transmitter configured to transmit X-rays at a predetermined angle, among the X-rays scattered by the scatterer.

19 Claims, 9 Drawing Sheets

(51) Int. Cl.
| | |
|---|---|
| *A61B 6/06* | (2006.01) |
| *A61B 6/42* | (2024.01) |
| *G21K 1/02* | (2006.01) |
| *G21K 1/10* | (2006.01) |

(56) References Cited

U.S. PATENT DOCUMENTS

| | | | | |
|---|---|---|---|---|
| 5,648,997 | A * | 7/1997 | Chao | A61B 6/405 |
| | | | | 378/98.12 |
| 5,684,851 | A * | 11/1997 | Kurbatov | G01N 23/046 |
| | | | | 378/154 |
| 6,054,712 | A * | 4/2000 | Komardin | G01V 5/222 |
| | | | | 250/363.1 |
| 6,175,615 | B1 * | 1/2001 | Guru | G21K 1/02 |
| | | | | 378/154 |
| 6,438,210 | B1 * | 8/2002 | Castleberry | G21K 1/025 |
| | | | | 378/154 |
| 7,020,237 | B2 * | 3/2006 | Francke | A61B 6/06 |
| | | | | 378/23 |
| 7,200,201 | B2 * | 4/2007 | Unger | A61B 6/4291 |
| | | | | 378/150 |
| 7,203,274 | B2 * | 4/2007 | Charles, Jr | A61B 6/482 |
| | | | | 378/54 |
| 7,356,126 | B2 * | 4/2008 | Bacher | G21K 1/00 |
| | | | | 378/154 |
| 7,368,151 | B2 * | 5/2008 | Souchay | G21K 1/025 |
| | | | | 378/154 |
| 7,397,888 | B2 * | 7/2008 | Sakuta | A61B 6/032 |
| | | | | 378/19 |
| 7,639,777 | B2 * | 12/2009 | Warner | G21K 1/025 |
| | | | | 378/19 |
| 7,945,015 | B2 * | 5/2011 | Tsujii | A61B 6/4028 |
| | | | | 378/124 |
| 8,139,717 | B2 * | 3/2012 | Harding | G21K 1/025 |
| | | | | 378/147 |
| 8,238,521 | B2 * | 8/2012 | McKim | G21K 1/025 |
| | | | | 378/149 |
| 8,262,288 | B2 * | 9/2012 | Shaughnessy | A61B 6/585 |
| | | | | 378/207 |
| 8,265,228 | B2 * | 9/2012 | Shaw | G21K 1/025 |
| | | | | 378/154 |
| 8,290,121 | B2 * | 10/2012 | Wirth | G21K 1/025 |
| | | | | 378/149 |
| 8,340,246 | B2 * | 12/2012 | Kang | A61B 6/4291 |
| | | | | 378/146 |
| 8,391,577 | B2 * | 3/2013 | Takahashi | G06T 5/73 |
| | | | | 378/7 |
| 8,831,180 | B2 * | 9/2014 | Hsieh | A61N 5/10 |
| | | | | 378/150 |
| 8,861,683 | B2 * | 10/2014 | Ding | G21K 1/067 |
| | | | | 359/809 |
| 8,891,727 | B2 * | 11/2014 | Kurochi | A61B 6/4208 |
| | | | | 378/19 |
| 8,995,615 | B2 * | 3/2015 | Yamaguchi | H05G 1/70 |
| | | | | 378/62 |
| 9,213,005 | B2 * | 12/2015 | Minot | G21K 1/025 |
| 9,239,304 | B2 * | 1/2016 | Yamaguchi | A61B 6/4035 |
| 9,848,840 | B2 * | 12/2017 | Ohashi | A61B 6/06 |
| 10,213,177 | B2 * | 2/2019 | Takahashi | A61B 6/461 |
| 10,722,196 | B2 * | 7/2020 | Yamazaki | A61B 6/032 |
| 10,794,845 | B2 * | 10/2020 | Filsinger | G01N 23/2076 |
| 10,980,494 | B2 * | 4/2021 | Lu | A61B 6/502 |
| 11,229,411 | B2 * | 1/2022 | Wiets | A61B 6/06 |
| 11,276,881 | B2 * | 3/2022 | Terai | H01B 1/10 |
| 11,517,273 | B2 * | 12/2022 | Lee | A61B 6/42 |
| 11,864,932 | B2 * | 1/2024 | Singh | A61B 6/032 |
| 12,064,275 | B2 * | 8/2024 | Ohashi | A61B 6/4441 |
| 12,336,850 | B2 * | 6/2025 | Kobayashi | A61B 6/06 |
| 12,364,446 | B2 * | 7/2025 | Mervin | A61B 6/4007 |
| 2012/0163552 | A1 | 6/2012 | Ding | |

FOREIGN PATENT DOCUMENTS

| | | | | | |
|---|---|---|---|---|---|
| JP | | 4118535 | B2 | 7/2008 | |
| JP | | 2014050737 | A * | 3/2014 | A61B 6/00 |
| JP | | 5723432 | B2 | 5/2015 | |
| JP | | 2015-198783 | A | 11/2015 | |
| JP | | 2016-131805 | A | 7/2016 | |
| JP | | 2020-18846 | A | 2/2020 | |
| JP | | 2020-56684 | A | 4/2020 | |
| JP | | 2021-10541 | A | 2/2021 | |

OTHER PUBLICATIONS

An English translation of JP2003018463A by Patent Translate (Year: 2024).*

Jay Theodore Cremer Jr., Advances in Imaging and Electron Physics, Chapter 4—X-ray Optics, vol. 172, 2012, pp. 497-559. (Year: 2012).*

Diana Adlienė, 2. Radiation interaction with condensed matter (Year: 2017).*

Office Action issued Sep. 10, 2025, in corresponding Japanese Patent Application No. 2021-192395, 3 pages.

Office Action issued Feb. 12, 2026, in corresponding Japanese Patent Application No. 2021-192395, citing documents 1-5 therein, 5 pages.

* cited by examiner

101

102 d1

101

102 d2

STRUCTURE FOR FORMING A PARALLEL X-RAY BEAM, X-RAY DIAGNOSTIC APPARATUS, AND METHOD

CROSS-REFERENCE TO RELATED APPLICATIONS

This application is based upon and claims the benefit of priority from Japanese Patent Application No. 2021-192395, filed on Nov. 26, 2021; the entire contents of which are incorporated herein by reference.

FIELD

Embodiments described herein relate generally to a structure, an X-ray diagnostic apparatus, and a method.

BACKGROUND

An X-ray diagnostic apparatus is an apparatus for acquiring an X-ray image depicting the internal structure of a subject by causing an X-ray emitter to irradiate the subject with X-rays, and causing an X-ray detector to detect the X-rays transmitted through the subject. Generally speaking, the X-rays emitted from the X-ray emitter often form a cone beam. For example, when an X-ray tube is installed as the X-ray emitter, the X-rays are emitted in a fan-like shape diverging from an X-ray focal point positioned at the anode of the X-ray tube.

When an X-ray image is captured using a cone X-ray beam, the magnification of the region included in the X-ray image of the subject changes depending on a source-to-image-receptor distance (SID) and a source-to-object distance (SOD).

Specifically, the magnification becomes higher with a shorter SID or SOD. When the region included in the X-ray image is a lesion, such a change in the magnification may become a cause of an overestimation or an underestimation of the lesion.

DETAILED DESCRIPTION

Figure 1:
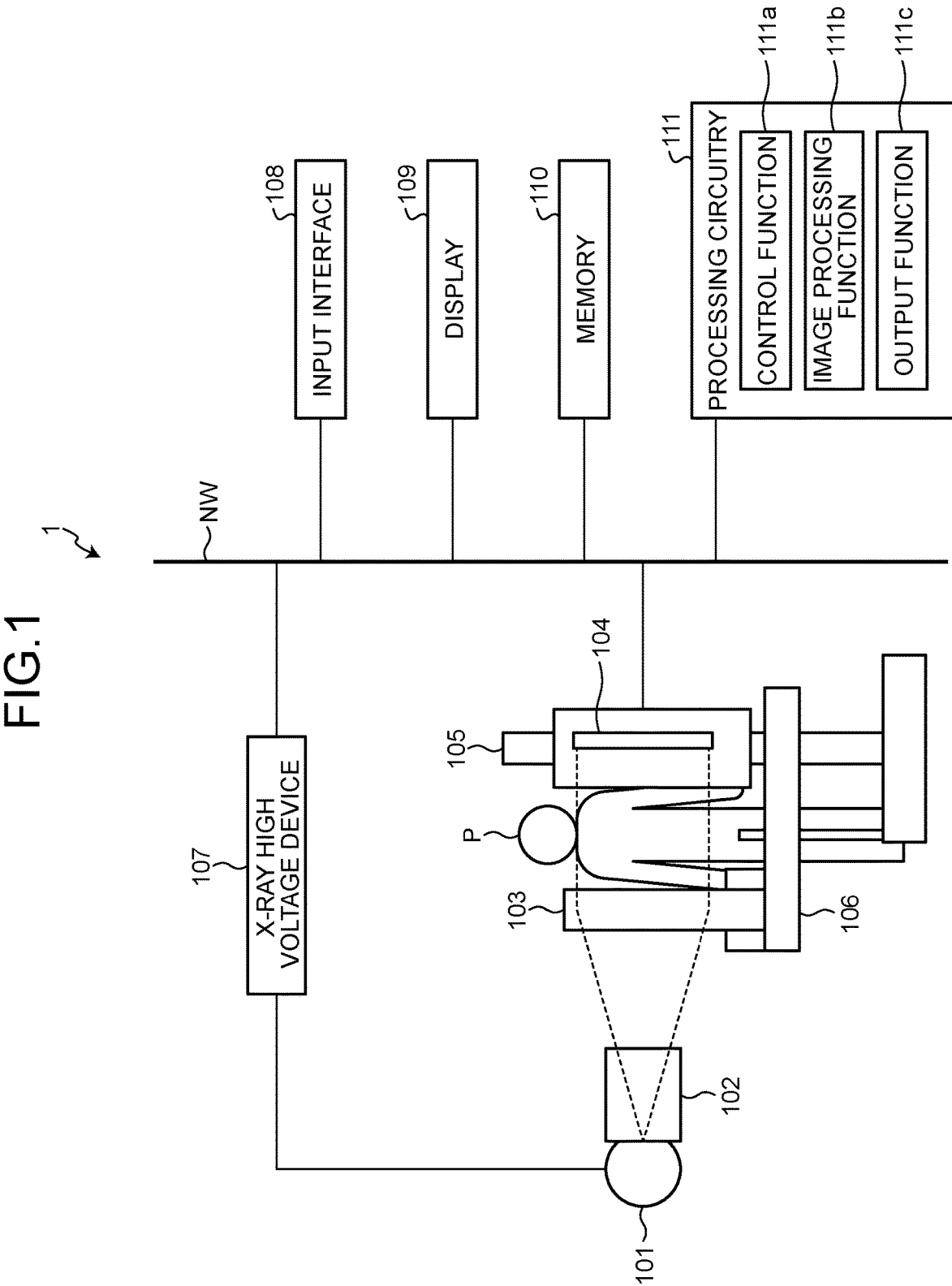
FIG. 1 is a block diagram illustrating an example of a configuration of an X-ray diagnostic apparatus according to a first embodiment.

Embodiments will now be explained in detail with reference to some drawings.

A configuration of an X-ray diagnostic apparatus 1 will now be explained with reference to FIG. 1. The X-ray diagnostic apparatus 1 includes an X-ray tube 101, an X-ray aperture 102, a structure 103, an X-ray detector 104, a stand 105, a holder 106, an X-ray high voltage device 107, an input interface 108, a display 109, a memory 110, and processing circuitry 111.

The X-ray tube 101 is an example of an X-ray emitter. The X-ray tube 101 is a vacuum tube with a cathode having a filament and an anode having a target. The X-ray tube 101 generates X-rays by emitting thermal electrons from the filament toward the target, and causing the thermal electrons to collide with the target, using the high voltage applied by the X-ray high voltage device 107. The X-ray high voltage device 107 applies a high voltage to the X-ray tube 101 under the control of the processing circuitry 111.

The X-ray aperture 102 includes, for example, aperture blades for demarcating a range to be irradiated with the X-rays emitted from the X-ray tube 101. The aperture blades are made of an X-ray shielding material such as lead and tungsten. The X-ray aperture 102 has four aperture blades, for example. With such a configuration, the X-rays emitted from the X-ray tube 101 travel through the X-ray aperture 102 formed by the four aperture blades, and the subject P is irradiated with the X-rays. In the example illustrated in FIG. 1, the X-ray aperture 102 controls the range to be irradiated with the X-rays emitted from the X-ray tube 101, and the structure 103 is irradiated with the resultant X rays.

The structure 103 is positioned between the X-ray tube 101 and the subject P, and enables the subject P to be irradiated with a parallel X-ray beam. The structure 103 will be described later in detail.

The X-ray detector 104 is an example of an X-ray detector. The X-ray detector 104 is an X-ray flat panel detector (FPD), for example. The X-ray detector 104 detects the X-rays emitted from the X-ray tube 101 and transmitted through the X-ray aperture 102, the structure 103, and the subject P. The X-ray detector 104 provides a detection signal corresponding to a detected X-ray dose to the processing circuitry 111.

The stand 105 is a mechanism that supports some or all of the components included in the X-ray diagnostic apparatus 1, when an image of the subject P who is standing is to be captured. In FIG. 1, the stand 105 supports the structure 103, the X-ray detector 104, and the holder 106. The holder 106 is mounted on the stand 105, and is a mechanism that supports the structure 103. With the holder 106, the structure 103 is integrated with the X-ray detector 104. The stand 105 and the holder 106 are examples of a support.

The input interface 108 is provided as a mouse, a keyboard, a trackball, a switch, a button, a joystick, a touchpad enabling an input operation to be made by touching the operation surface, a touchscreen that is an integration of a display screen and a touchpad, a non-contact input circuitry using an optical sensor, and a voice input circuitry, for example. The input interface 108 receives various input operations from a user, and supplies electrical signals corresponding to the received input operations to the processing circuitry 111.

The display 109 is provided as a display device, such as a liquid crystal display or a cathode ray tube (CRT) display. The display 109 displays various types of information supplied from the processing circuitry ill.

The memory 110 is a storage device including, for example, a random access memory (RAM), a semiconductor memory element such as a flash memory, a hard disk, or an optical disc. The memory 110 stores therein various types of information supplied from the processing circuitry 111. The memory 110 also stores therein a computer program to be executed by the processing circuitry 111.

The processing circuitry 111 is implemented as an arithmetic processing unit such as a central processing unit (CPU) and a micro-processing unit (MPU). For example, the processing circuitry 111 functions as a control function 111a, an image processing function 111b, and an output function 111c, by reading and executing computer programs stored in the memory 110. The image processing function 111b is an example of an image processing unit.

The control function 111a, for example, controls an irradiation of the subject P with X-rays. Specifically, the control function 111a controls to supply a high voltage from the X-ray high voltage device 107 to the X-ray tube 101, and controls to open the aperture in the X-ray aperture 102.

The image processing function 111b generates an X-ray image of the subject P based on the X-rays detected by the X-ray detector 104, for example. Specifically, the X-ray detector 104 outputs the detection signal corresponding to an X-ray dose detected thereby, and the image processing function 111b generates an X-ray image using the detection signal received from the X-ray detector 104.

The output function 111c displays the X-ray image generated by the image processing function 111b on the display 109, or sends the X-ray image to an external image storage device so as to store therein the X-ray image, for example.

The X-ray diagnostic apparatus 1 having the configuration described above irradiates the subject P with a parallel X-ray beam. With this, an SID- or SOD-dependent change in the magnification can be avoided, and this contributes to an improvement in the accuracy of interpretations of the image, and to reductions in the sizes of the apparatus and examination room.

Figure 2:
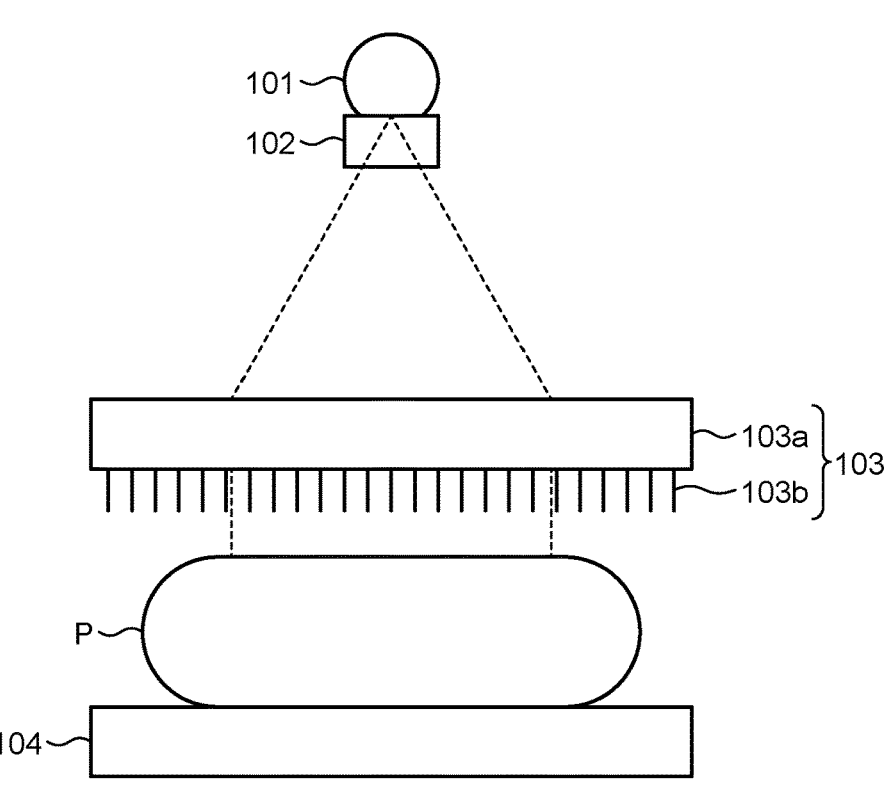
FIG. 2 is a schematic for explaining an emission of a parallel X-ray beam in the first embodiment.

An emission of a parallel X-ray beam by the X-ray diagnostic apparatus 1 will now be explained with reference to FIG. 2. In FIG. 2, the X-rays emitted from the X-ray tube 101 are illustrated in the dashed lines. As illustrated in FIG. 2, the X-rays emitted from the X-ray tube 101 diverge as a cone beam, and, by transmitting through the structure 103, the X-rays turn into a parallel X-ray beam, and the subject P is irradiated therewith.

Figure 3:
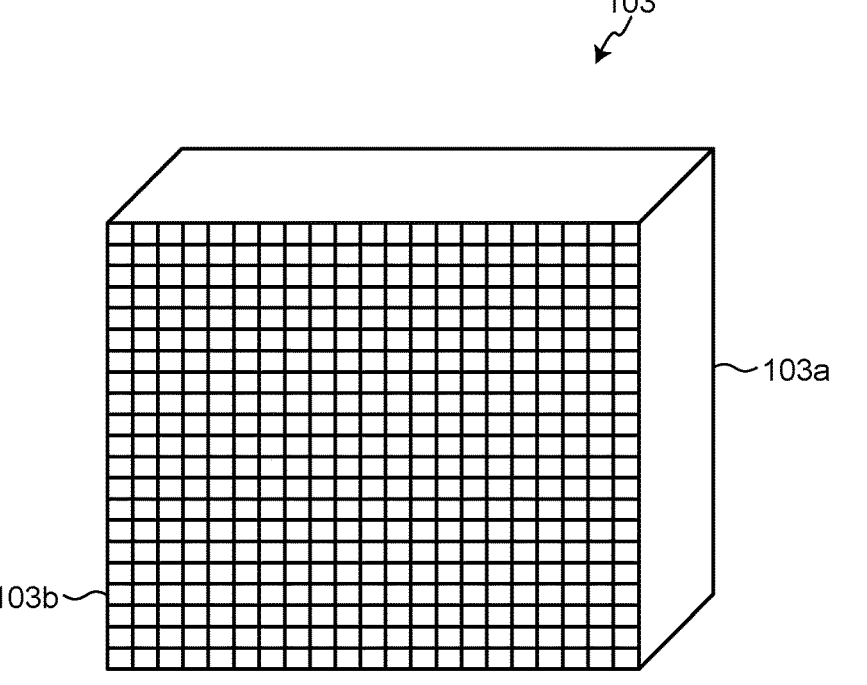
FIG. 3 is a schematic for illustrating an example of a structure according to the first embodiment.

As illustrated in FIGS. 2 and 3, the structure 103 includes an acrylic material 103a and a grid 103b. The acrylic material 103a is an example of a scatterer, and scatters the X-rays emitted from the X-ray tube 101. The grid 103b is an example of a transmitter, and transmits X-rays at a predetermined angle, among those scattered by the acrylic material 103a. For example, the grid 103b includes an arrangement of a plurality of plate-like members that are made of an X-ray shielding material, and that are arranged in parallel with each other along a predetermined direction.

Although the acrylic material 103a is used as an example of a scatterer, any material may be selected as long as the material is capable of scattering X-rays. In FIG. 3, although a cross grid that is an intersecting grid is used as the transmitter, the embodiment is not limited thereto. For example, as the transmitter, grid 103b may be provided with a honeycomb grid including a honeycomb-like (hexagonal) grid.

Figure 4:
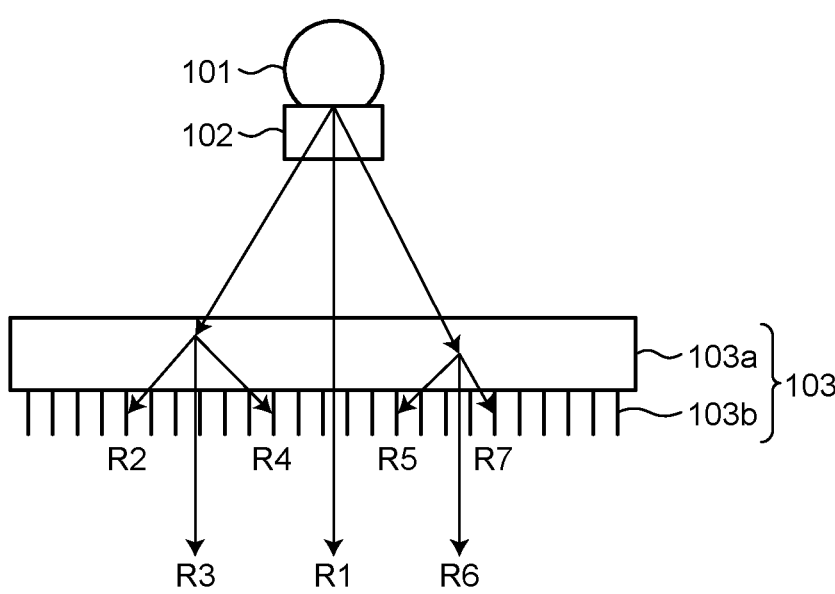
FIG. 4 is a schematic for explaining an emission of a parallel X-ray beam in the first embodiment.

The structure 103 will now be explained more in detail with reference to FIG. 4. As illustrated in FIG. 4, the X-rays emitted from the X-ray tube 101 diverge as a cone beam, and become incident at different angles on the acrylic material 103a.

At this time, as illustrated as the X-ray R1 in FIG. 4, for example, some of the X-rays having become incident on the acrylic material 103a are transmitted through the acrylic material 103a and the grid 103b, and the subject P is irradiated therewith. In other words, because the grid 103b is structured to transmit X-rays at a predetermined angle, an X-ray R1 having become incident on the acrylic material 103a at the predetermined angle and transmitted through the acrylic material 103a can transmit through the grid 103b.

By contrast, as illustrated as X-rays R2 and R7 in FIG. 4, for example, some of the X-rays having become incident on the acrylic material 103a are blocked by the grid 103b, after transmitting through the acrylic material 103a. In other words, the X-rays R1 having become incident on the acrylic material 103a at an angle different from the predetermined angle and having been transmitted through the acrylic material 103a cannot transmit through, and are blocked by the grid 103b.

Some of the X-rays having become incident on the acrylic material 103a are scattered by the acrylic material 103a, as illustrated as X-rays R3, R4, R5 and R6 in FIG. 4, for example. Among these scattered X-rays, those that are scattered in the predetermined angle, such as the X-rays R3 and R6, can transmit through the grid 103b. The X-rays having scattered in angles different from the predetermined angle, such as the X-rays R4 and R5, cannot transmit through the grid 103b, and are blocked thereby.

As illustrated in FIG. 4, only the X-rays at the predetermined angle, such as the X-rays R1, R3, and R6, transmit through the grid 103b, so that a parallel beam is formed thereby. In other words, the structure 103 makes it possible to irradiate the subject P only with components perpendicular to the subject P, among those included in the cone X-ray beam and its scattered X-rays.

Figure 5:
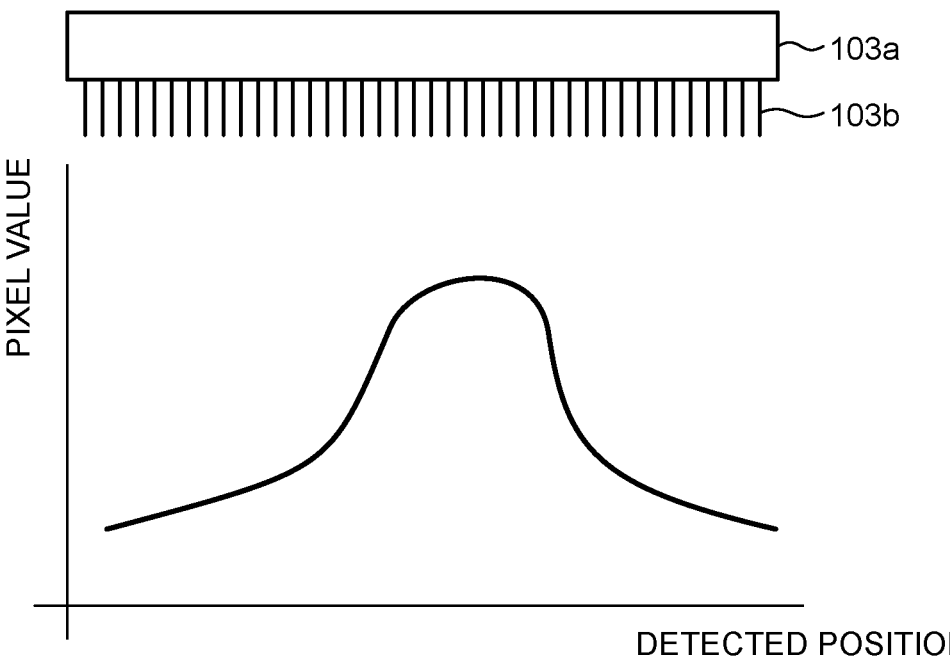
FIG. 5 is a schematic illustrating a pixel value distribution according to the first embodiment.

At this time, compared with the X-ray R1, the X-ray R3 and the X-ray R6 take long paths to transmit through the acrylic material 103a, and therefore, are subjected to greater attenuations. Among the scattered X-rays, the X-rays R3 and R6 are scattered components scattered in the predetermined angle, and have low coefficient rates, compared with those of the components transmitted through the acrylic material 103a and the grid 103b without being scattered, e.g., X-ray R1. Therefore, the X-ray detector 104 detects a higher X-ray dose in the central region that includes the X-ray axis (the path of the X-ray R1 in FIG. 4), and detects a lower X-ray dose at a position further away from the central region. The X-ray energy distribution also becomes varied due to the effect of a change in the X-ray energy during the scattering process, and due to the effect of beam hardening. The resultant X-ray image generated therefrom therefore has higher pixel values in the central region, and the pixel values are lower at positions further away from the central region, as illustrated in FIG. 5.

Figure 6:
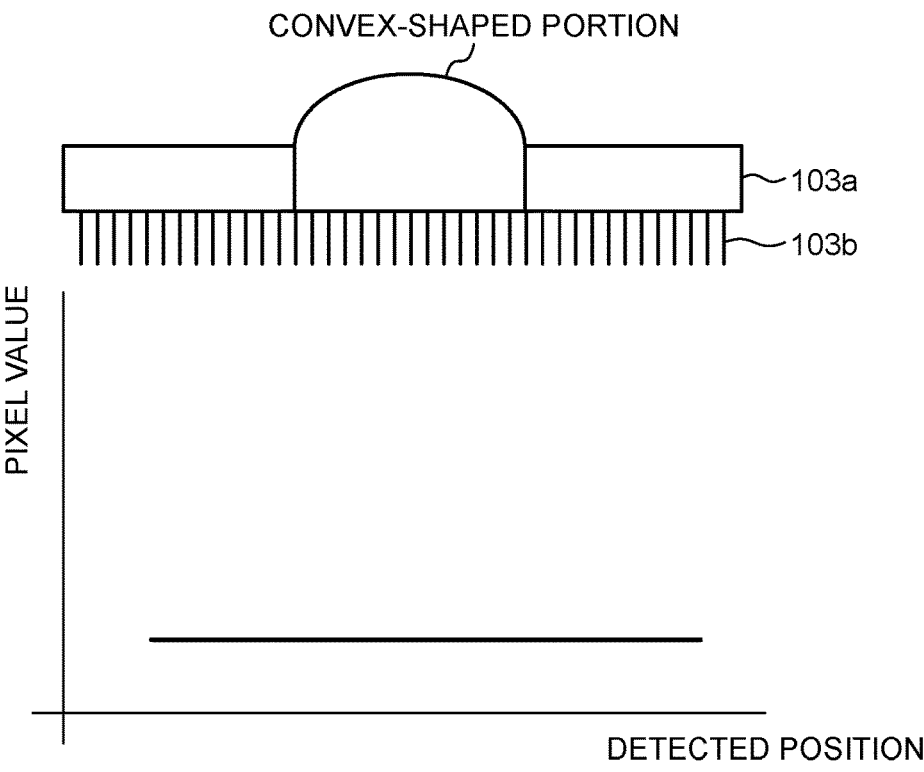
FIG. 6 is a schematic illustrating a pixel value distribution according to the first embodiment.

Hence, the acrylic material 103a may be configured to have a convex-shaped portion on an incidence surface where the X-rays emitted from the X-ray tube 101 become incident, as illustrated in FIG. 6. In the configuration illustrated in FIG. 6, the X-rays being incident on the central region of the X-ray detector 104 are caused to attenuate to approximately the same X-ray dose level as those of X-rays being incident on the positions away from the central region. As a result, it is possible to suppress variations in the pixel values, the variations being those that are dependent on the detected positions in the generated X-ray image. In other words, the pixel value distribution in the X-ray image can be flattened.

Figure 7:
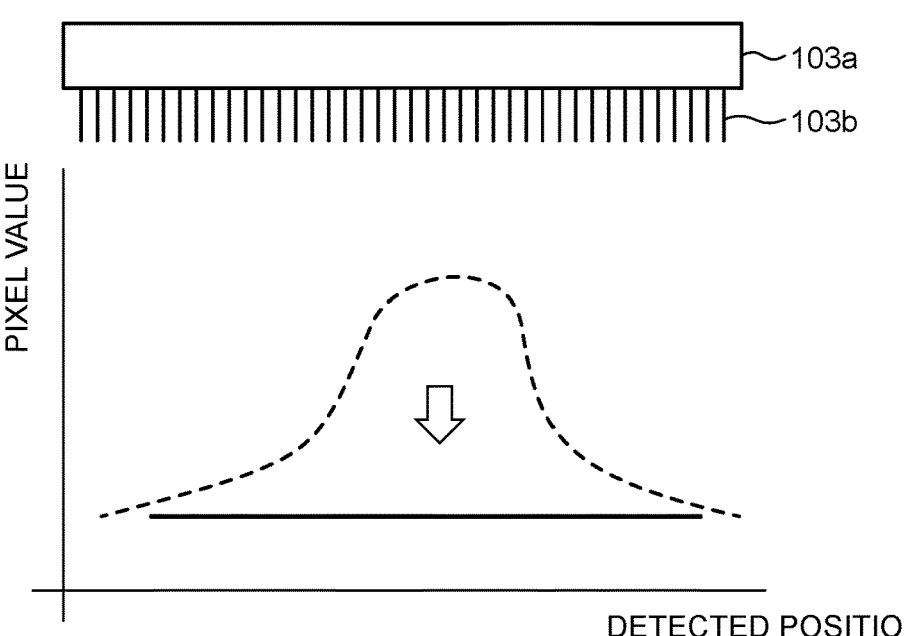
FIG. 7 is a schematic illustrating a pixel value distribution according to the first embodiment.

Alternatively, as illustrated in FIG. 7, the image processing function 111b may apply a correction for eliminating a systematic error in the pixel values corresponding to the respective detected positions, to the X-ray image. In other words, a systematic error in an X-ray dose distribution or an X-ray energy distribution is estimable, e.g., the X-ray dose of the X-ray R1 is higher than those from the X-ray R3 or the X-ray R6. Based on such an estimation, the image processing function 111b can perform a correction for eliminating the systematic error in the pixel values in the X-ray image.

For example, the image processing function 111b can perform a correction for eliminating the systematic error in the pixel values corresponding to the respective detected positions based on a correction X-ray image (calibration image) captured in advance. Such a correction X-ray image is captured without the subject P placed between the X-ray tube 101 and the X-ray detector 104. Such a correction X-ray image is data representing the extraction of the systematic error in an X-ray dose distribution or an X-ray energy distribution, with the effect of transmission through the subject P eliminated. The correction X-ray image may be captured for each condition, e.g., a tube voltage or a tube current for the X-ray tube 101, the degree by which the X-ray aperture 102 is opened, an SID, or an SOD. The memory 110 may store therein the correction X-ray images captured for these different conditions, respectively. To correct an X-ray image captured from a subject P, the image processing function 111b can make a correction for eliminating the systematic error in the pixel values at the respective detected positions by using a correction X-ray image captured under the same condition as the X-ray image to be corrected.

By providing the structure 103, the dose of X-rays with which the subject P is irradiated becomes reduced. This is because some of the X-rays emitted from the X-ray tube 101 are absorbed or scattered by the acrylic material 103a or blocked by the grid 103b. Taking this reduction of the X-ray dose into consideration, the output from the X-ray tube 101 may be set high, or a sensitive X-ray detector 104 may be provided, compared with those used when the structure 103 is not provided.

As described above, the structure 103 is disposed between the X-ray tube 101 and the subject P. The acrylic material 103a scatters the X-rays emitted from the X-ray tube 101. Among the X-rays scattered by the acrylic material 103a, the grid 103b transmits the X-rays at the predetermined angle.

With this, the structure 103 according to the embodiment can emit X-rays in the form of a parallel beam.

It is also possible to capture an X-ray image using a cone X-ray beam, instead of a parallel X-ray beam. However, in such a case, the magnification of the region included in the X-ray image of the subject changes depending on the SID or the SOD.

Figure 8A:
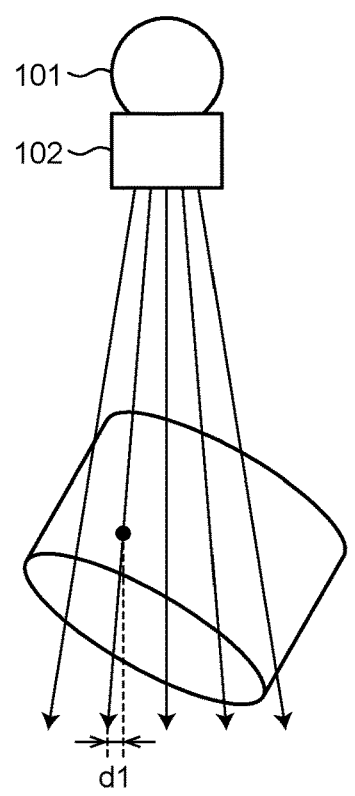
FIG. 8A is a schematic for explaining a magnification according to the first embodiment.
Figure 8B:
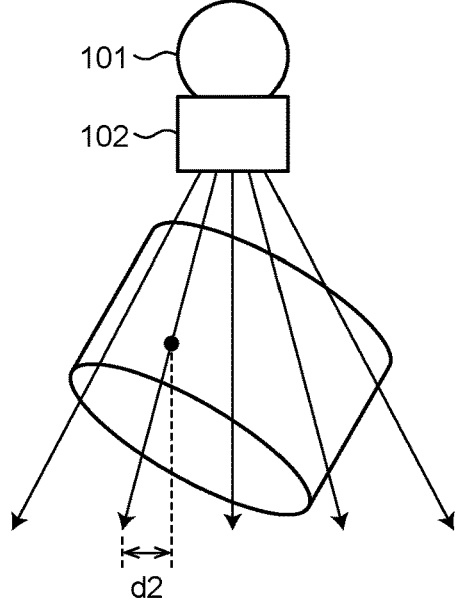
FIG. 8B is a schematic for explaining the magnification according to the first embodiment.

FIG. 8A illustrates an example in which there is a long distance (SOD) between the X-ray tube 101 and the region included in the X-ray image. FIG. 8B illustrates an example in which the SOD is short. In the X-ray images to be captured in the examples illustrated in FIGS. 8A and 8B, the regions included in the X-ray images are enlarged to sizes larger than the actual size, by the differences in the distance indicated by "d1" and "d2", respectively. The magnification of the region included in the X-ray image changes depending on the SID or the SOD, and, when the region included in the X-ray image is a lesion, for example, such a change may result in an overestimation or an underestimation of the lesion.

To suppress the effect of magnification while using a cone X-ray beam, for example, it is possible to ensure a longer SID or SOD, as illustrated in FIG. 8A. However, even in the case illustrated in FIG. 8A, the effect of the magnification is not eliminated. In addition, because a longer SID or SOD is translated into an increase in the size of the apparatus, and also into an increase in the size of the examination room where the apparatus is installed, it is disadvantageous from the viewpoint of costs.

By contrast, by enabling the X-rays to be emitted in the form of a parallel beam using the structure 103, it is possible to eliminate the effect of magnification and to improve the accuracy of interpretations. In addition, the sizes of the apparatus and the examination room can be reduced because there is no need to extend the SID or the SOD.

In a second embodiment, modifications related to the configuration of the X-ray diagnostic apparatus 1 will be explained.

In FIG. 1, the structure 103 has been explained to be supported by the holder 106 mounted on the stand 105. However, there are various possible modifications of the mechanism for supporting the structure 103.

Figure 9:
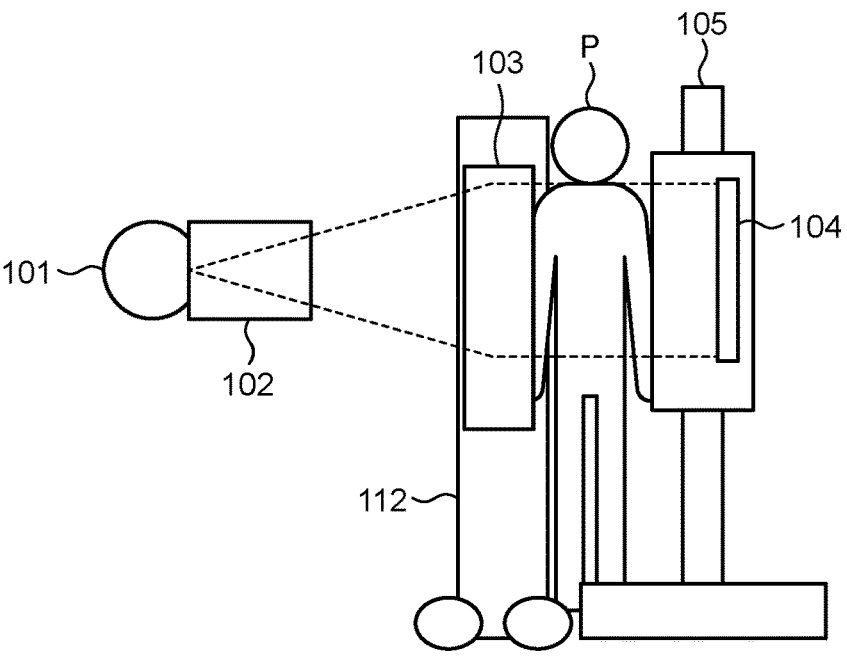
FIG. 9 is a block diagram illustrating an example of a configuration of an X-ray diagnostic apparatus according to a second embodiment.

For example, the X-ray diagnostic apparatus 1 may be provided with a stand 112 instead of the holder 106, as illustrated in FIG. 9. In the example illustrated in FIG. 9, the structure 103 can be moved independently from the X-ray detector 104, and positioned between the X-ray tube 101 and the subject P, like a partitioning screen. The stand 112 is an example of the support.

Figure 10:
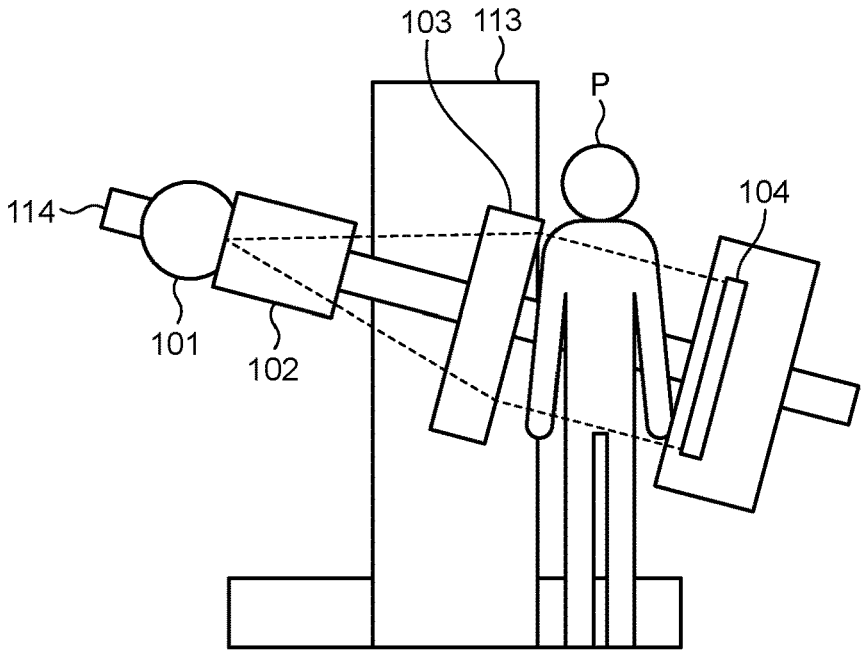
FIG. 10 is a block diagram illustrating an example of a configuration of an X-ray diagnostic apparatus according to a second embodiment.

The X-ray diagnostic apparatus 1 may also be provided with a stand 113 and an arm 114, as illustrated in FIG. 10, instead of the holder 106. The stand 113 supports the arm 114. The arm 114 supports the X-ray tube 101, the X-ray aperture 102, the structure 103, and the X-ray detector 104. With the arm 114, the structure 103 is integrated with the X-ray detector 104. With the arm 114, the structure 103 is also integrated with the X-ray tube 101. In this configuration, the stand 113 supports the arm 114 rotatably, so that the X-ray diagnostic apparatus 1 can irradiate the subject P with a parallel X-ray beam at any angle. The stand 113 and the arm 114 are examples of the support.

Explained in FIGS. 1, 9, and 10 is an example in which the subject P who is standing is irradiated with X-rays, but the posture of the subject P is not limited thereto. For example, the X-ray diagnostic apparatus 1 may be configured to irradiate the subject P who is lying with the X-rays, as illustrated in FIGS. 11 and 12.

Figure 11:
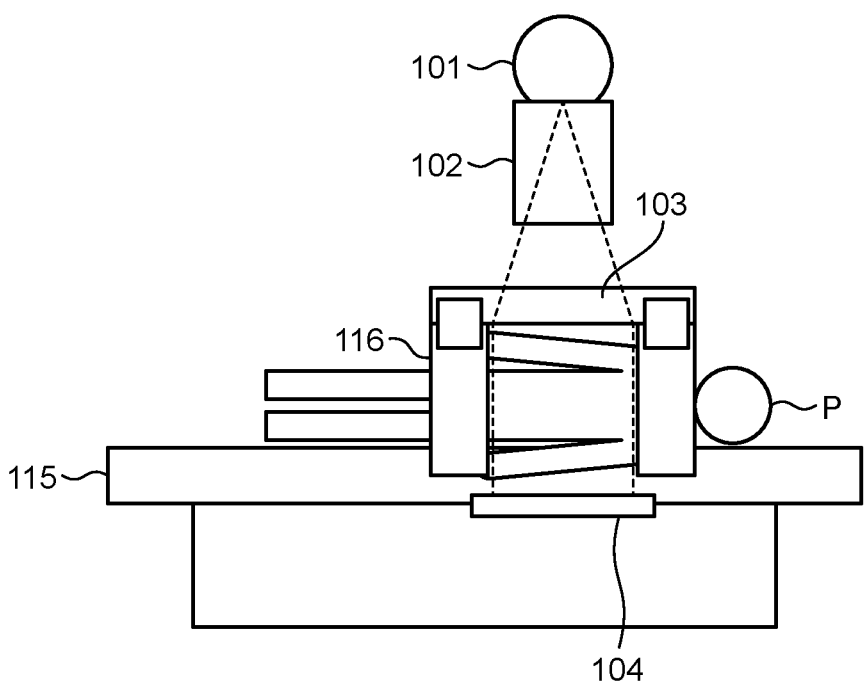
FIG. 11 is a block diagram illustrating an example of a configuration of an X-ray diagnostic apparatus according to a second embodiment.

In the example illustrated in FIG. 11, the X-ray diagnostic apparatus 1 is provided with a couch 115 and arms 116. The subject P is placed in a lying position on the couch 115. The arms 116 support the structure 103. The arms 116 are mounted on the couch 115, or placed on the couch 115, for example. The arms 116 are an example of the support.

Figure 12:
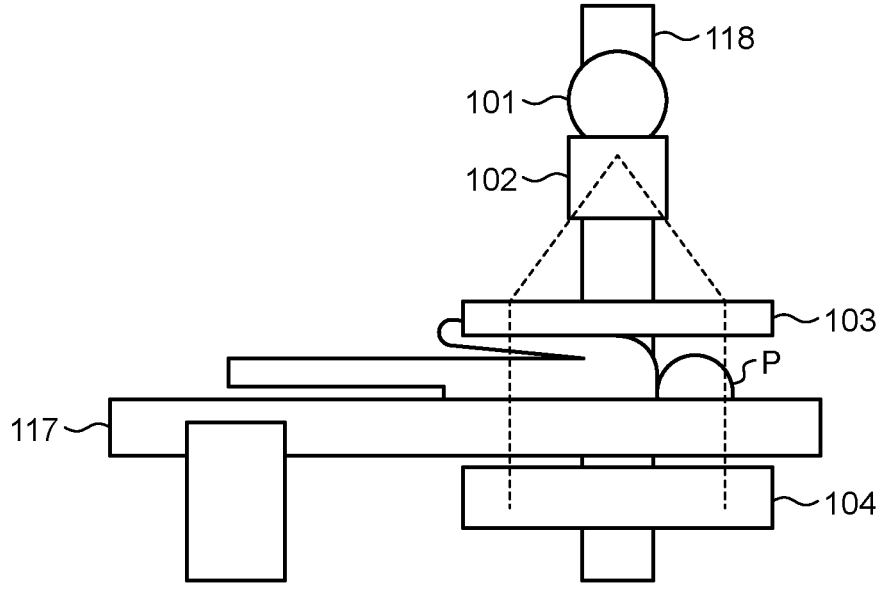
FIG. 12 is a block diagram illustrating an example of a configuration of an X-ray diagnostic apparatus according to a second embodiment.

In the example illustrated in FIG. 12, the X-ray diagnostic apparatus 1 is provided with a couch 117 and an arm 118. The subject P is laid in a lying position on the couch 117. The arm 118 supports the X-ray tube 101, the X-ray aperture 102, the structure 103, and the X-ray detector 104. With the arm 118, the structure 103 is integrated with the X-ray detector 104. With the arm 118, the structure 103 is also integrated with the X-ray tube 101. The arm 118 is an example of the support.

Figure 13:
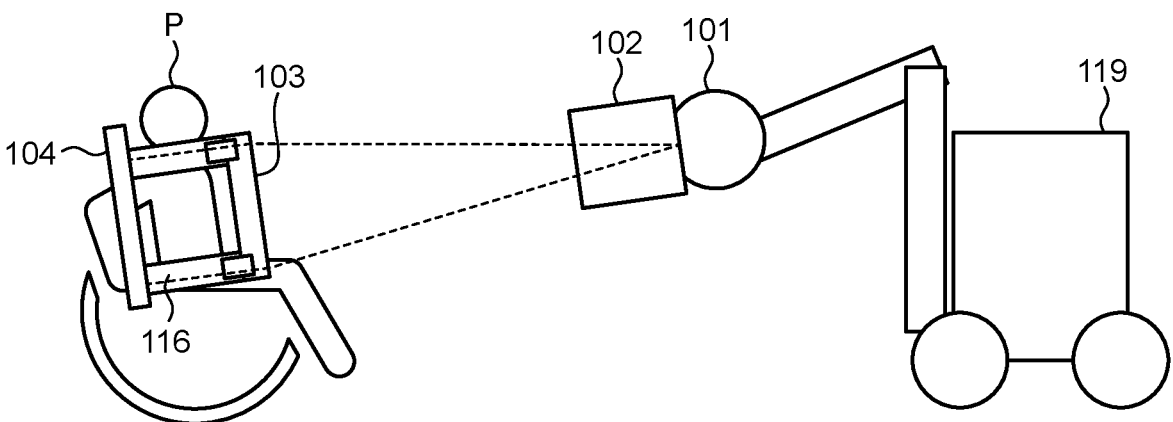
FIG. 13 is a block diagram illustrating an example of a configuration of an X-ray diagnostic apparatus according to a second embodiment.

The X-ray diagnostic apparatus 1 may also be configured to irradiate the subject P who is seated with the X-rays, as illustrated in FIG. 13. In the example illustrated in FIG. 13, the X-ray diagnostic apparatus 1 is provided with a ward round trolley 119. The ward round trolley 119 supports the X-ray tube 101 and the X-ray aperture 102 in a movable manner. The X-ray diagnostic apparatus 1 is also provided with a mechanism for supporting the structure 103, such as the arms 116.

Figure 14:
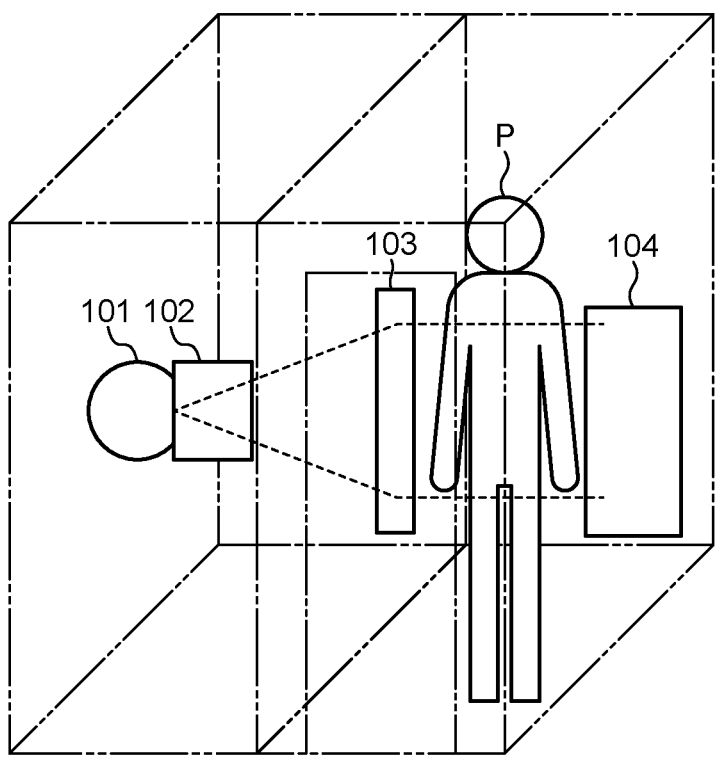
FIG. 14 is a block diagram illustrating an example of a configuration of an X-ray diagnostic apparatus according to a second embodiment.

The X-ray diagnostic apparatus 1 may also be disposed in a small examination room, as illustrated in FIG. 14. As described above, because the X-ray diagnostic apparatus 1 including the structure 103 does not have the problem with the magnification, and does not need to extend the SID or the SOD, it is possible to reduce the size of the examination room.

Explained in a third embodiment is an example in which an X-ray image is captured by scanning the range to be included in the X-ray image. In other words, explained below is an example in which an X-ray image is captured by irradiating a part of the range to be included in the X-ray image of the subject P with X-rays, while shifting the position being irradiated with the X-rays, instead of capturing the X-ray image by irradiating the entire range to be included in the X-ray image all at the same time with the X-rays.

Figure 15:
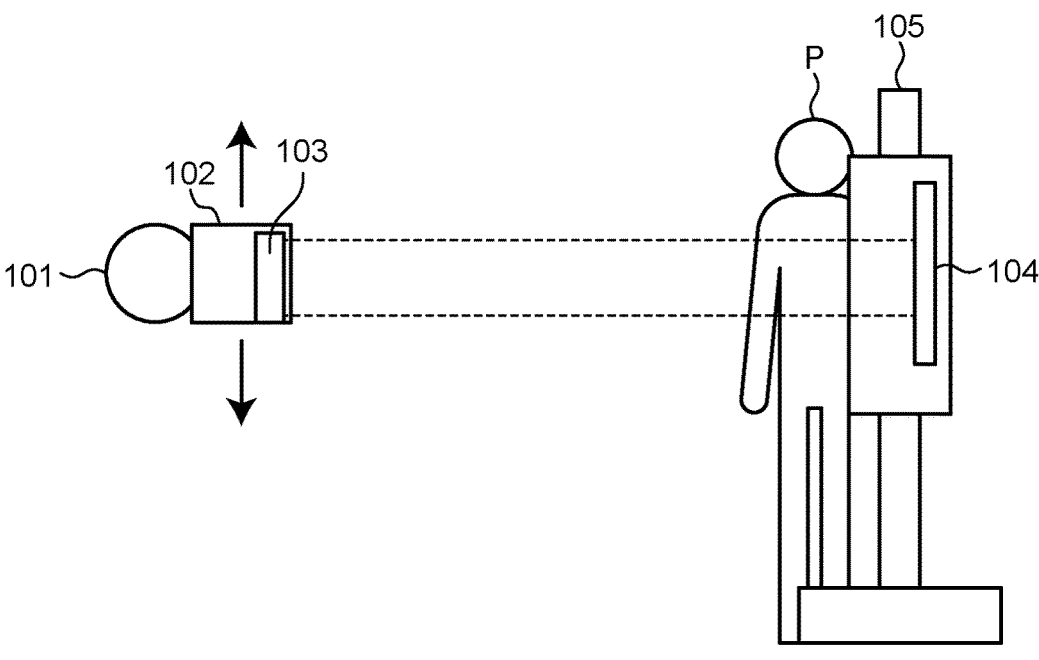
FIG. 15 is a block diagram illustrating an example of a configuration of an X-ray diagnostic apparatus according to a third embodiment.

FIG. 15 is a block diagram illustrating an example of a configuration of the X-ray diagnostic apparatus 1 according to the third embodiment. The X-ray tube 101, the X-ray aperture 102, and the structure 103 are supported by a support mechanism not illustrated, in a manner movable in the directions of the arrows in FIG. 15. In other words, as illustrated in the dotted lines in FIG. 15, the X-rays transmitted through the structure 103 are turned into a parallel beam, and the subject P is irradiated therewith. More specifically, by causing the grid 103b in the structure 103 to transmit the X-rays at the predetermined angle, X-rays that are parallel with the predetermined angle are emitted. The X-ray tube 101, the X-ray aperture 102, and the structure 103 are configured to be movable in directions orthogonal to the predetermined angle.

In FIG. 15, the structure 103 is illustrated as being integrated with the X-ray aperture 102. For example, in the example illustrated in FIG. 15, the structure 103 is built into the X-ray aperture 102. With this, it is possible to reduce the sizes of the structure 103, the support mechanism, and the like. The aperture opening in the X-ray aperture 102 demarcates the range to be irradiated with the parallel X-ray beam. Thus, sometimes the range to be irradiated with the X-rays may become smaller than the range to be included in the X-ray image in the subject P.

Figure 16:
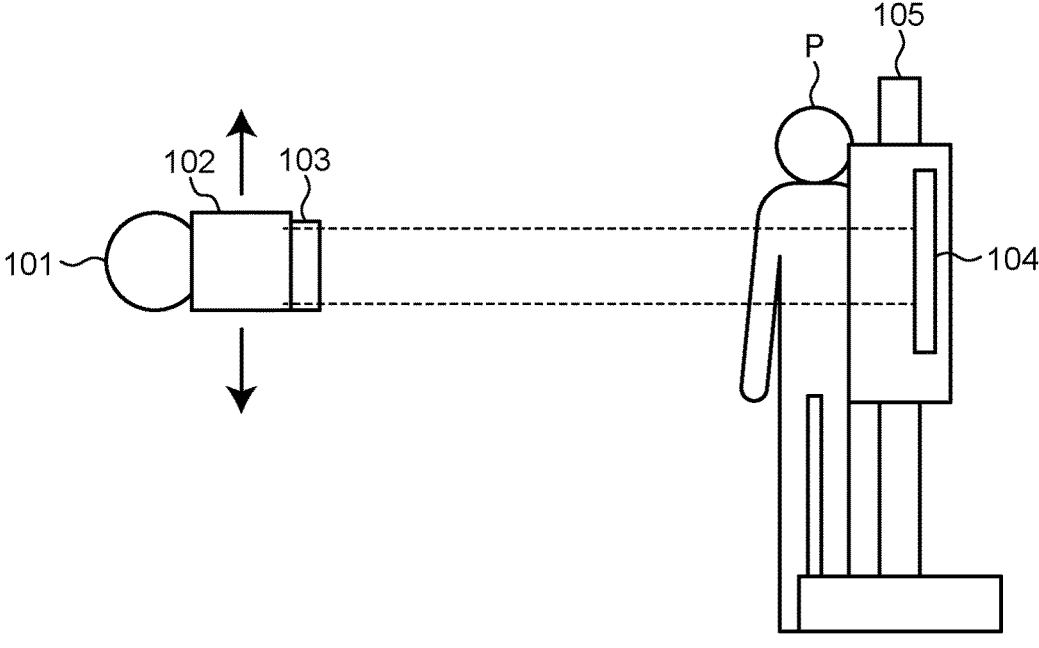
FIG. 16 is a block diagram illustrating an example of the configuration of the X-ray diagnostic apparatus according to the third embodiment.

Therefore, the X-ray diagnostic apparatus 1 moves the X-ray tube 101, the X-ray aperture 102, and the structure 103 in the directions indicated by the arrows in FIG. 15. With this, by shifting the position irradiated with the X-rays, the X-ray diagnostic apparatus 1 can irradiate the entire range to be included in the X-ray image with the X-rays, and captures an X-ray image corresponding to the entire range to be included in the X-ray image. The same can be said when the structure 103 is disposed in front of the X-ray aperture 102, as illustrated in FIG. 16.

The term "processor" used in the above explanation means circuitry such as a CPU, a graphics processing unit (GPU), an application-specific integrated circuit (ASIC), and a programmable-logic device (e.g., a simple programmable-logic device (SPLD), a complex programmable-logic device (CPLD), and a field programmable-gate array (FPGA)). If the processor is a CPU, for example, the processor implements a function by reading and executing a computer program stored in a memory. If the processor is an ASIC, for example, instead of storing the computer program in a memory, the function is directly incorporated into the processor circuit, as a logic circuit. The processors in the embodiment are not limited to a configuration in which each of the processors is implemented as a single circuit, but may also have a configuration in which a combination of a plurality of independent circuits are configured as a single processor, and the function may be implemented thereby. Furthermore, the function may be implemented by integrating a plurality of elements in the drawings into a single processor.

It has been explained so far that a single memory stores therein computer programs corresponding to the respective processing functions of the processing circuitry. However, embodiments are not limited thereto. For example, a plurality of memories may be deployed in a distributed manner, and the processing circuitry may be configured to read the computer programs from the respective memories. Instead of storing the computer programs in a memory, it is also possible to use a configuration in which the computer programs are directly incorporated into the processor circuitry. In such a case, the processor implements the functions by reading and executing the computer programs incorporated in the circuitry.

The elements included in each of the apparatuses according to the embodiments described above are functional and conceptual representations, and do not necessarily need to be physically configured as illustrated in the drawings. In other words, the specific configurations in which the apparatuses are distributed or integrated are not limited to those illustrated in the drawings, and may also be configured by functionally or physically distributing or integrating the whole or a part of the apparatuses in any units, based on various loads and utilization conditions. Furthermore, the processing functions executed by each of the apparatus may be implemented, in whole or in part, as a CPU and a computer program parsed and executed by the CPU, or as hardware using wired logic.

The method explained in the embodiments described above may also be implemented by causing a computer such as a personal computer or a workstation to execute a computer program. This computer program may be distributed over a network such as the Internet. The computer program may also be recorded a computer-readable non-transitory recording medium such as a hard disk, a flexible disk (FD), a compact disc read-only memory (CD-ROM), a magneto-optical disk (MO), and a digital versatile disc (DVD), and executed by causing a computer to read the computer program from the recording medium.

According to at least one of the embodiments described above, it is possible to emit X-rays as a parallel beam.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A structure that is disposed between an X-ray emitter and a subject, the structure comprising:

a scatterer made of a material capable of scattering X-rays and transmitting the scattered X-rays, the scatterer being configured to scatter X-rays emitted from the X-ray emitter, wherein the scattering of the X-rays by the material is either Compton scattering or Thomson scattering; and a transmitter configured to transmit X-rays at a single, predetermined angle, among the X-rays scattered by the scatterer, wherein the scatterer has a convex-shaped portion on an incidence surface, where the X-rays emitted from the X-ray emitter become incident.

2. The structure according to claim 1, wherein the material is an acrylic material.

3. An X-ray diagnostic apparatus, comprising:

an X-ray emitter configured to emit X-rays;

a structure provided between the X-ray emitter and a subject; and an X-ray detector configured to detect X-rays transmitted through the structure, wherein the structure includes:

a scatterer made of a material capable of scattering X-rays and transmitting the scattered X-rays, the scatterer being configured to scatter the X-rays emitted from the X-ray emitter, wherein the scattering of the X-rays by the material is either Compton scattering or Thomson scattering; and a transmitter configured to transmit X-rays at a single, predetermined angle, among the X-rays scattered by the scatterer, wherein the scatterer has a convex-shaped portion on an incidence surface, where the X-rays emitted from the X-ray emitter become incident.

4. The X-ray diagnostic apparatus according to claim 3, further comprising processing circuitry configured to generate an X-ray image of the subject based on the X-rays detected by the X-ray detector.

5. The X-ray diagnostic apparatus according to claim 4, wherein the processing circuitry is further configured to perform a correction for eliminating a systematic error in pixel values at respective detected positions in the X-ray image.

6. The X-ray diagnostic apparatus according to claim 5, wherein the processing circuitry is further configured to apply the correction to the X-ray image based on a correction X-ray image captured without the subject placed between the X-ray emitter and the X-ray detector.

7. The X-ray diagnostic apparatus according to claim 3, further comprising a support configured to support the structure.

8. The X-ray diagnostic apparatus according to claim 7, wherein the structure is integrated with the X-ray detector.

9. The X-ray diagnostic apparatus according to claim 7, wherein the structure is integrated with the X-ray emitter.

10. The X-ray diagnostic apparatus according to claim 3, further comprising an X-ray aperture configured to control a range to be irradiated with the X-rays emitted from the X-ray emitter, wherein the structure is configured to transmit X-rays resulting from the X-ray aperture having controlled the range to be irradiated with the X-rays emitted from the X-ray emitter.

11. The X-ray diagnostic apparatus according to claim 10, wherein the structure is built into the X-ray aperture or disposed in front of the X-ray aperture.

12. The X-ray diagnostic apparatus according to claim 10, wherein the range to be irradiated with the X-rays is smaller than a range to be included in an X-ray image of the subject, and the X-ray emitter, the structure, and the X-ray aperture are shifted in a direction orthogonal to the single, predetermined angle so as to irradiate the range to be included in the X-ray image with the X-rays.

13. A method, comprising:

emitting X-rays from an X-ray emitter; and detecting, with an X-ray detector, X-rays at a single predetermined angle from the emitted X-rays that are (1) scattered by a scatterer made of a material capable of scattering X-rays and transmitting the scattered X-rays, and (2) transmitted through a transmitter, wherein the scattering of the X-rays by the material is either Compton scattering or Thomson scattering, wherein the scatterer has a convex-shaped portion on an incidence surface, where the X-rays emitted from the X-ray emitter becomes incident.

14. The method according to claim 13, wherein the X-ray detector is configured to detect X-rays at the single, predetermined angle, the X-rays having been scattered by the scatterer and transmitted through the transmitter, among the X-rays emitted from the X-ray emitter, and the method further comprises generating an X-ray image of a subject based on the X- rays detected by the X-ray detector.

15. The method according to claim 14, further comprising applying, to the X-ray image, a correction for eliminating a systematic error in pixel values corresponding to respective detected positions.

16. The method according to claim 15, further comprising applying the correction to the X-ray image based on a correction X-ray image captured without the subject placed between the X-ray emitter and the X-ray detector.

17. The method according to claim 14, wherein a structure including the scatterer and the transmitter is supported by a support.

18. The method according to claim 17, wherein the structure is integrated with the X-ray detector.

19. The method according to claim 17, wherein the structure is integrated with the X-ray emitter.

* * * * *